US012567485B1

(12) United States Patent
Swenson

(10) Patent No.: US 12,567,485 B1
(45) Date of Patent: Mar. 3, 2026

(54) ADDRESS ENHANCEMENT

(71) Applicant: IQVIA Inc., Parsippany, NJ (US)

(72) Inventor: Karen Swenson, Bedford, NH (US)

(73) Assignee: IQVIA INC., Durham, NC (US)

( * ) Notice: Subject to any disclaimer, the term of this patent is extended or adjusted under 35 U.S.C. 154(b) by 95 days.

(21) Appl. No.: 18/405,878

(22) Filed: Jan. 5, 2024

Related U.S. Application Data

(60) Provisional application No. 63/472,610, filed on Jun. 13, 2023, provisional application No. 63/437,595, filed on Jan. 6, 2023.

(51) Int. Cl.
*G06F 16/00* (2019.01)
*G16H 10/60* (2018.01)
(52) U.S. Cl.
CPC .................................... *G16H 10/60* (2018.01)
(58) Field of Classification Search
CPC ................................ G06F 16/00; G16H 10/60
See application file for complete search history.

(56) References Cited

U.S. PATENT DOCUMENTS

| | | | |
|---|---|---|---|
| 8,782,025 B2 | 7/2014 | Swenson | |
| 2013/0080181 A1* | 3/2013 | DePetro | G06Q 10/10 |
| | | | 705/2 |
| 2023/0073347 A1* | 3/2023 | Ginsburg | G16H 15/00 |

* cited by examiner

*Primary Examiner* — Cheryl Lewis
(74) *Attorney, Agent, or Firm* — Troutman Pepper Locke LLP

(57) ABSTRACT

A method and system obtain records for a health care provider from sources, each record specifying an address for the health care provider. An accuracy score to each address is assigned based on (i) relationships among some of the records for the health care provider or (ii) applicability, to the address, of an accuracy trend for the source of the address. The accuracy score for each of the addresses is adjusted based on applying audit rules to the address, each audit rule specifying an adjustment to the accuracy score based on a value in the record for the address satisfying or violating the audit rule. The addresses for the health care provider and rankings are stored. A ranking for an address is determined based on the relative adjusted accuracy scores of the address. Data indicative of the address rankings can be displayed on a user interface.

20 Claims, 4 Drawing Sheets

300

```
┌──────────────────────────────────────────────────┐
│ OBTAIN RECORDS FOR A HEALTHCARE PROVIDER FROM      │  ⌐ 310
│ ONE OR MORE SOURCES, EACH RECORD SPECIFYING        │
│ AN ADDRESS FOR THE HEALTHCARE PROVIDER             │
└──────────────────────────────────────────────────┘
                        │
                        ▼
┌──────────────────────────────────────────────────┐
│ ASSIGN AN ACCURACY SCORE TO EACH ADDRESS           │  ⌐ 320
│ BASED ON (i) RELATIONSHIPS AMONG THE MULTIPLE      │
│ RECORDS OR (ii) APPLICABILITY OF AN ACCURACY       │
│ TREND FOR THE SOURCE OF THE ADDRESS                │
└──────────────────────────────────────────────────┘
                        │
                        ▼
┌──────────────────────────────────────────────────┐
│ ADJUST ACCURACY SCORE FOR EACH ADDRESS BASED       │  ⌐ 330
│ ON APPLYING AUDIT RULES                            │
└──────────────────────────────────────────────────┘
                        │
                        ▼
┌──────────────────────────────────────────────────┐
│ STORE THE ADDRESSES FOR THE HEALTHCARE             │  ⌐ 340
│ PROVIDER AND A RANKING FOR EACH OF THE             │
│ ADDRESSES IN A DATA STORAGE OF THE COMPUTER        │
│ SYSTEM                                             │
└──────────────────────────────────────────────────┘
                        │
                        ▼
┌──────────────────────────────────────────────────┐
│ PROVIDE, FOR DISPLAY ON A USER INTERFACE, DATA     │  ⌐ 350
│ INDICATIVE OF THE RANKING OF THE ADDRESSES         │
└──────────────────────────────────────────────────┘
```

FIG. 3

ADDRESS ENHANCEMENT

CROSS-REFERENCE TO RELATED APPLICATIONS

This application claims the benefit of U.S. Provisional Patent Application No. 63/437,595, filed Jan. 6, 2023, and U.S. Provisional Patent Application No. 63/472,610, filed Jun. 13, 2023, which are incorporated herein by reference in their entirety.

BACKGROUND

A compilation of addresses of potential and existing customers is an important asset for any company that uses traditional methods to identify, manage and allocate the multiple types of addresses that are configured for a professional to meet multiple operational needs for customer management, personal and non-personal communications. However, it can be a daunting task to keep a large compilation of addresses up-to-date and accurate.

A person often has multiple addresses of different types or categories. These addresses can enter into private or public records through many channels, for example, state or federal government authorizations, licensing or certification, membership in professional associations, registration of real property or motor vehicles, posting in advertisements, etc. After the addresses become available in these original sources, they can later be transferred to, shared or purchased by myriads of organizational entities including the government, communities, or commercial vendors (these become "secondary sources" for the addresses).

The reliability of some of these sources can be questionable, as they are typically not actively monitored. For example, when a person changes his or her address, the change often is likely reflected in only a few of the above sources at the outset (and can percolate through other sources at different times). As a result, many sources, especially the secondary sources, can contain a significant portion of outdated addresses.

A user may want to gather the addresses of the persons of interest from various sources. However, the use of multiple address sources does not guarantee a broader reach to the targeted audience, but instead can create confusion and cause more waste. This is due to not only the varying reliability of the individual sources, but also the conflicts or inconsistencies of the addresses provided by the different sources. For example, an address can be present in one source, but not another; a person can have multiple office addresses reported by different sources, yet no information is available as to which one is more current. Without further analysis or investigation, a user of such addresses will not be able to use them effectively.

SUMMARY

The systems and methodologies described below assess the currency and reliability of addresses obtained from various sources, as well as to reconcile the inconsistencies and conflicts of a large number of addresses from records obtained through different sources of healthcare provider information. The systems and methodologies assist with presenting the analyzed addresses to a user in an understandable format to allow the user to more reliably and effectively use the addresses for a range of commercial applications, e.g., in the healthcare space. A computing system can be configured to analyze addresses from records for a healthcare provider obtained from the different sources. The analysis includes an identification of relationships between records from different sources, and/or an identification of accuracy trends for or stratifications within a source of the address. The analysis includes an assignment of a preliminary accuracy score based on the identified relationships and/or accuracy trends. Audit rules are applied to adjust the accuracy score for the address and permit a ranking of addresses based on the adjusted accuracy score of the address for the healthcare provider, which can be captured, tracked over time, and stored in data storage.

Data indicating the ranking of the addresses can be provided for display on a user interface and can be used within various types of decision systems (delivery systems, operational systems, transactional systems, clinical systems, master data management systems) to determine which addresses are suitable for use within the range of applications for a life sciences company. For example, a pharmaceutical company may use addresses of a particular rank as a factor in a variety of activities including, to set territory alignments, deploy sales representatives for targeting healthcare provider (HCP) outreach or drug sampling, to define the scope of intended HCPs for a regional marketing campaign or inclusion in a clinical trial being conducted in a specific locale, to comply with transparency reporting or as a factor in sales representative compensation by territory. The values for address ranking, if sufficiently accurate, can be used by life sciences companies to maintain their database management systems and drive day-to-day operational decisions as to where health care professionals are currently located and participating within the health care industry.

The assignment of accuracy scores for addresses associated with a healthcare provider includes evaluating the different sources of address data for trends that can indicate an accuracy of the address. The assignment of an accuracy score can be based on an evaluation of records from multiple sources, such as identifying combinations of sources that result in enhanced (e.g., relative to a single source) address information for the healthcare provider. The assignment of an accuracy score for an address can also include an identification of accuracy trends of a particular source, thereby making use of a historical accuracy of a source to readily process additional updates to addresses and/or records.

The accuracy scores for an address for a healthcare provider can be adjusted by audit rules applied to the initial accuracy score of the address. In some cases, audit rules can be evidence-based through evidence data collected from user devices and database management systems. The evidence data can include validation conducted by data analysts, who may perform research to identify the validity of an address associated to a healthcare provider. In other cases, the audit rules are evidence or business rule based through analysis of incremental factors lending positive or negative credence to the basic information presented by the source. Thus, the analysis of evidence and/or healthcare provider records allows for a holistic accuracy enhancement of addresses for healthcare providers.

A computing system can receive large volumes (e.g., tens of millions) of addresses associated with numerous healthcare providers (e.g., millions) on a regular basis (e.g., daily, weekly). Because some of these disparate addresses are stale, conflicting, duplicative, or inaccurate, even from widely reported sources, there are significant operational and sales inefficiencies and compliance risks for a life sciences company, e.g., if the sales force is attempting to market to, conduct sales calls upon or drop off drug samples for healthcare professionals at old or inaccurate locations.

For individual life science companies to have to overcome, through trial and error, the challenges and accuracy issues across the varied sources is time consuming, costly, inefficient, error prone, and risky given the nature of tracking compliance with FDA rules and state rules governing compliance regulations and transparency. Further, the continual process of providing updates to databases of the computing system with poor quality addresses (e.g., stale, conflicting, duplicative, inaccurate) results in extraneous consumption of computing resources and increased processing loads to service the updates. Thus, the ranking and accuracy tracking of addresses from records across different sources of address data for healthcare providers permits the exclusion of some addresses from particular sources. Reducing and/or preventing updates from particular sources with records of inaccurate address can result in fewer updates of an internal database of the computing system, thus resulting in a reduction of computing resources.

Improvements to address accuracy results in an increase in output data quality for end users, as address data can be provided to healthcare organizations, pharmaceutical companies, research institutions, and/or other parties interested in healthcare provider data. The increased accuracy and tracking of healthcare provider addresses allow end users to consistently execute efficient targeting, drug trials, compliance, and sales and marketing operations by providing valuable information as to an accurate location of a healthcare professional for the full spectrum of activities and usages by the life sciences industry. Further, the ranked address information can be presented to a user, e.g., through a graphical user interface of a device.

For example, providing accurate information to parties interested in healthcare provider data can improve targeting of pharmaceutical products and information to healthcare providers through improved communication with healthcare providers, e.g., using an accurate address from these disclosed techniques. The improvements reduce the likelihood of address data provided to the end users being low quality, e.g., an address indicating that a healthcare provider practices in a state where they do not practice or provide care. As another example, these improvements also provide guidance for address tracking for healthcare providers that practice telehealth medicine across a large range of states and addresses and help identify telehealth locations of their practice. Another example would be overcoming the inaccuracies of key public sources which represent false positive address data or alternative, limitations from sources which often allow mid-level professionals to opt out of releasing address information, which could lead to false negative indications.

The techniques described in this specification can be referred to as address intelligence enhancements, which allow for efficient processing and updating of addresses from external sources. The external sources include reference files representing records of addresses for healthcare providers. The address intelligence enhancements described in this specification can achieve advantages such as reducing the rate of false positives, e.g., instances when an address is incorrectly assigned as an active address, when the address is inactive. As another example, an advantage of the address intelligence enhancement also includes reducing rates of false negatives, e.g., instances when an address is indicated as transitional or old, when the address is current for a healthcare provider.

Other advantages provided by the address enhancements can include increasing consistency in aligning affiliations between healthcare providers to respective addresses and organizations. The address intelligence enhancements also provide increased accuracy of analyzed addresses and improved stability of the enhanced addresses, such as reducing likelihoods of addresses being extraneously updated between two different statuses, e.g., current and non-current. For example, audit rules can be applied to mitigate addresses extraneous switching between two statuses unless a particular type of evidence is provided indicated that an address status can be overridden.

In one general aspect a method performed by a computing system includes obtaining, by the at least one processor of the computer system, multiple records for a health care provider from one or more sources, each record specifying an address for the health care provider. The method includes assigning, by the at least one processor, an accuracy score to each address based on (i) relationships among at least some of the multiple records for the health care provider or (ii) applicability, to the address, of an accuracy trend for the source of the address. The method includes adjusting, the at least one processor, the accuracy score for each one or more of the addresses based on applying one or more audit rules to the address, each audit rule specifying an adjustment to the accuracy score based on a value in the record for the address satisfying or violating the audit rule. The method includes storing, in a data storage of the computing system, the addresses for the health care provider and a ranking for each of the addresses, the ranking determined based on the relative adjusted accuracy scores of the addresses and providing, for display on a user interface, data indicative of the ranking of the addresses.

Other embodiments of this and other aspects of the disclosure include corresponding systems, apparatus, and computer programs, configured to perform the actions of the methods, encoded on computer storage devices. A system of one or more computers can be configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

The foregoing and other embodiments can each optionally include one or more of the following features, alone or in combination. For example, one embodiment includes all the following features in combination.

In some implementations, the method includes assigning the accuracy score to each address based further on an age of the address. In some implementations, the method includes determining the applicability of the accuracy trend to a given address based on a value in the record specifying the given address.

In some implementations, the accuracy trend for a source indicates a likelihood that an address from that source is accurate; and in which assigning the accuracy score for a particular address from a given source comprises determining the applicability of the likelihood for the given source to the particular address.

In some implementations, the method includes determining the relationships among the at least some of the multiple records by identifying a key value linking the records.

In some implementations, the method includes applying the one or more audit rules based on a type of each of the addresses.

In some implementations, the method includes identifying a type of each address. In some implementations, identifying the type of each address is based on evidence in the corresponding record indicative of the type of address. In some implementations, in the absence of evidence indicative of the type of address for a given address, the method includes categorizing the given address as an unknown type.

In some implementations, the method includes identifying the type of each address based on a rule specifying assessment of street front addresses. In some implementations, the method includes identifying the type of each address comprises resolving a conflict between multiple types of addresses identified for the address.

In some implementations, the method includes applying the one or more audit rules to a given address based on a type of occupation of the health care provider.

In an aspect, an address intelligence system includes a computing device that includes at least one process, and a memory communicatively coupled to the at least one processor, the memory storing instructions which, when executed by the at least one processor, cause the at least one processor to perform operations. The operations include obtaining, by the at least one processor, multiple records for a health care provider from one or more sources, each record specifying an address for the health care provider. The operations include assigning, by the at least one processor, an accuracy score to each address based on (i) relationships among at least some of the multiple records for the health care provider or (ii) applicability, to the address, of an accuracy trend for the source of the address. The operations include adjusting, the at least one processor, the accuracy score for each one or more of the addresses based on applying one or more audit rules to the address, each audit rule specifying an adjustment to the accuracy score based on a value in the record for the address satisfying or violating the audit rule. The operations include storing, in a data storage of the computing system, the addresses for the health care provider and a ranking for each of the addresses, the ranking determined based on the relative adjusted accuracy scores of the addresses, and providing, for display on a user interface, data indicative of the ranking of the addresses.

The details of one or more implementations are set forth in the accompanying drawings and the description below. Other features and advantages will be apparent from the description and drawings, and from the claims.

BRIEF DESCRIPTION OF THE DRAWINGS

FIG. 3 is a flow diagram that illustrates an example of a process for enhancing and ranking addresses from address data.

Like reference numbers and designations in the various drawings indicate like elements. The components shown here, their connections and relationships, and their functions, are meant to be examples only, and are not meant to limit the implementations described and/or claimed in this document.

DETAILED DESCRIPTION

Figure 1:
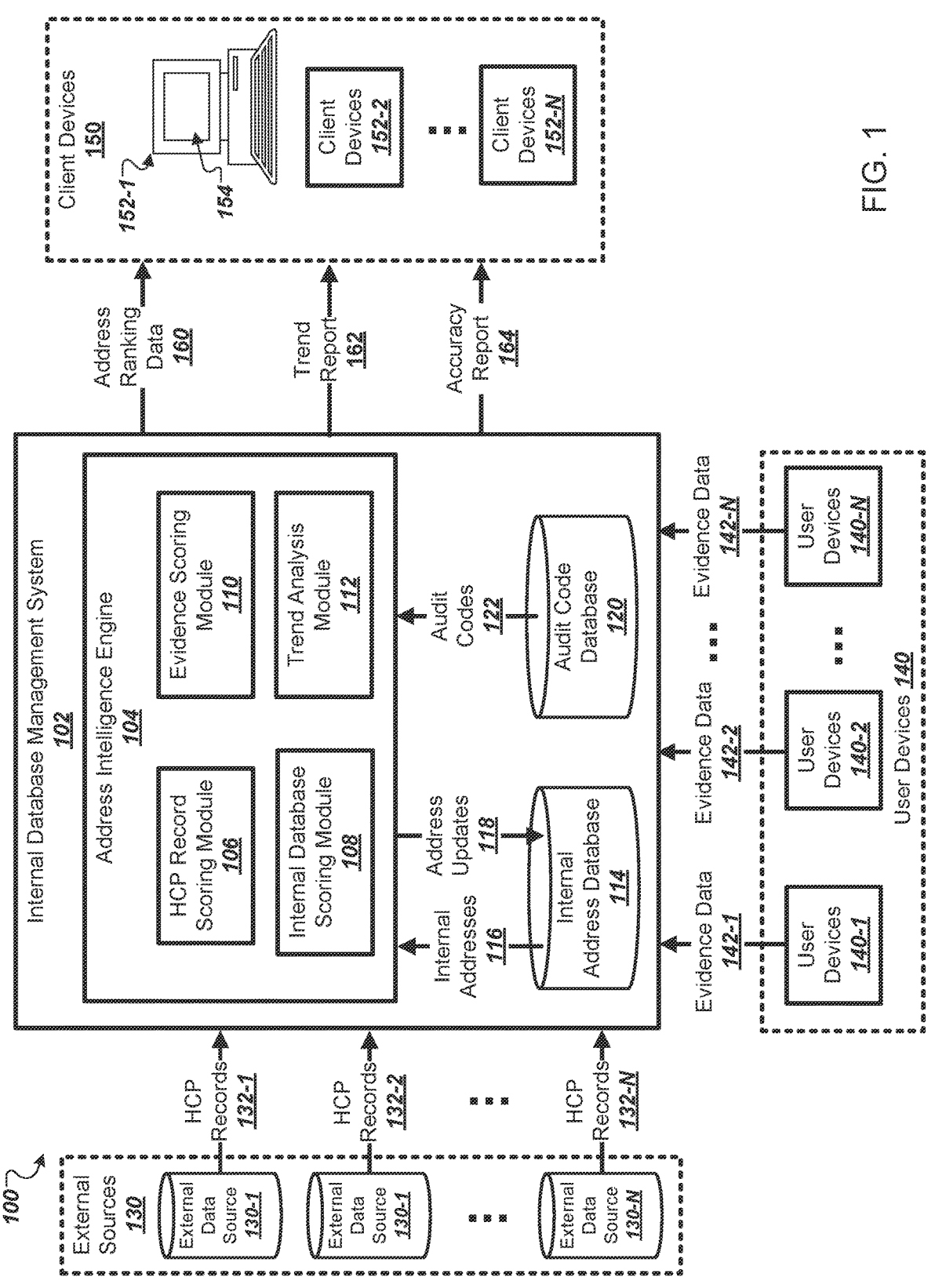
FIG. 1 is a block diagram that illustrates an example of a computing system determining and applying address enhancements from address data.

The described techniques herein include providing a user with one or more addresses of a person of interest, such as a healthcare provider or professional. The techniques are hereinafter referred to as the "address intelligence techniques." The address intelligence techniques are based on an analysis of the currency (e.g., an accuracy) of an occupancy (e.g., an address for the person of interest), the source(s) where the occupancy is obtained, as well as an evaluation of the occupancy (e.g., an address) based on a set of criteria designed using the characteristics of the occupancy, including characteristics of the sources that provided the occupancy. The techniques "score" an occupancy based on cumulative quantity of the occupancy reported by the various sources as well as the currency and quality of these sources. Such a score can be converted to a rank representing the degree of confidence with respect to currency of the address. The techniques also include assigning accuracy scores based on relationships between records of addresses between sources, and based on accuracy trends for addresses from a source. In situations where a person has multiple addresses, the technique can select the best address or addresses according to the rank, the indicator, or a combination of both, by adjusting the accuracy score for each address using audit rules that specify adjustments to the accuracy score for an address. The address intelligence techniques further allow the reconciliation of the inconsistencies found in large collections of occupancies reported from different sources, thus enabling more effective use of these occupancies.

Some computing systems can be configured to process data from different sources to obtain addresses for healthcare providers. When obtaining addresses from these sources, the computing system process large volumes of data that can be provided on a recurring basis (e.g., daily, weekly), resulting in millions of addresses processed by the computing system. However, sources for addresses can report inaccurate addresses for healthcare providers, which result in extraneous consumption of computing resources in obtaining addresses from the sources and wasted processing cycles when processing data for the addresses. An address with poor accuracy or representation of an actual practice location for a healthcare provider causes inefficiencies for recipients of healthcare provider addresses, such as service providers, healthcare organizations, and other interested parties for healthcare provider address data. An inaccurate address for a healthcare provider results in unsuccessful outreach to the healthcare provider, as well as extraneous attempts to reach the healthcare provider using inaccurate addresses.

An inaccurate address for a healthcare provider can be an outdated practice location (e.g., the healthcare provider no longer provides service at the address), a temporary practice location (e.g., the healthcare provider occasionally provides medical services at the particular location), as well as addresses associated with the healthcare provider's licensing or other types of certifications, among many reasons for inaccurate addresses in data sources. For example, addresses from different types of sources are updated at different cadences than one another, e.g., one source is updated annually while another source updates monthly. The techniques described in this specification utilize information about the data sources themselves, characteristics of the healthcare provider, relationships between the addresses in a data source or across data sources, as well as other related accuracy trends for addresses among sources, to process large amount of address data and identify accurate addresses for healthcare providers. In particular, the disclosed techniques determine likelihoods that an given address is a correct address for a healthcare provider, thereby increasing the likelihood of successful outreach to the healthcare provider. The identification of an accurate address can be particularly important to service providers that rely on addresses for activities that support healthcare treatment, such as dropping off samples from a laboratory, delivering unique types of medicine, organ transportation, etc.

As used in the present application, the word "person" includes a person whose address(es) is obtained and processed by the address intelligence techniques disclosed in the presently described subject matter. Certain aspects of the described subject matter are illustrated in the context of the healthcare industry where the person of interest can be a healthcare professional, e.g., a physician, an administrative contact of a healthcare organization, etc. The term "person" can include a prescriber who has prescription qualification (e.g., a physician), a mid-level practitioner (e.g., Nurse, Physician's Assistant), or more generally a "professional." The presently described techniques can be applied to persons of any category or industry and is not limited to persons in the healthcare industry.

The term "service provider" includes an individual or organization that may use the address intelligence techniques described herein to obtain, procedure, and present data for its customer(s). Service providers provides services to customers and can demand accurate address data to contact healthcare providers. An accurate address for a healthcare provider can permit a service provider to reach out to a healthcare provider, with fewer attempts to contact the healthcare provider compared to numerous attempts at addresses that the healthcare provider no longer uses. Examples of service providers include medical device companies, pharmaceutical companies, clinical trial organizations, and other entities that can support administration of healthcare to patients, medical research, etc.

The term "occupancy" includes a unique combination of an identifier of a person and an address of the person. As a name can be shared by many persons, a person can be represented by a unique identifier, such as SSN #, license number, etc. A person can have multiple different addresses, and they can be of different types (e.g., office, home, mailing, etc.). These different addresses for the same person can be referred to as different occupancies associated with the person. Note that one occupancy, e.g., "David Smith, 123 Main Street" can be reported multiple times by different sources. This can be referred to as the multiple instances of an occupancy, rather than different occupancies. An occupancy can include other attributes, such as the affiliation or specialty of a person, or the type or category of an address (e.g., home, office, etc.).

An occupancy can be obtained from one or more external and internal sources. "External sources," as used herein, include sources of occupancies that are not proprietary databases of the service provider. They include but are not limited to: reference files purchased or otherwise obtained from private data providers (e.g., healthcare organizations, research institutions, or pharmaceutical companies) or made publicly available by government agencies or public organizations (e.g., the Drug Enforcement Agency (DEA), National Provider Identifier (NPI), State License Number (SLN), professional associations). The reference files can also be referred to as "records" and/or "address records", which can be updated periodically, e.g., daily, weekly, or monthly, from the external sources. For example, a database management system of the service provider can be configured to obtain the records that include address data from the external sources at a particular cadence.

"Internal sources" include one or more proprietary databases maintained by a service provider, e.g., a research database internal to (e.g., maintained/administered by) the service provider for healthcare analysts. The research database can include multiple kinds of evidence collected by analysts, such as primary research, desk research, transactional data analysis, etc. and stores the different kinds of evidence as "address evidence data" (also referred to as "affiliation evidence data") for a database management system. It is understood that internal sources can operate similarly as the external sources. For example, an internal address database can be organized in a substantially similar fashion as external databases such as commercial and/or government databases. An occupancy (e.g., an address) can be obtained each of one or more sources, e.g., external sources only, internal sources only, or combinations thereof. Multiple instances of an occupancy associated with a single person can be obtained from multiple sources. Occupancy data can be obtained from internal sources and external sources, as described in U.S. Pat. No. 8,782,025, titled "Systems and Methods for Address Intelligence," filed as U.S. patent application Ser. No. 12/721,280 on 10 Mar. 2010 and issued on 15 Jul. 2014, the contents of which is incorporated by reference in its entirety.

Various type of systems and techniques can utilize this address information and related information, such as the systems described in U.S. Pat. No. 8,782,025, titled "Systems and Methods for Address Intelligence," filed as U.S. patent application Ser. No. 12/721,280 on 10 Mar. 2010 and issued on 15 Jul. 2014, the contents of which is incorporated by reference in its entirety. Such systems can provide additional functionality for processing addresses; for example, various type of rules (e.g., business rules, audit codes) can be implemented and utilized to enhance operations. In one arrangement, techniques may be employed to improve assignment of address terms (e.g., "Office", "PO Box"). Functionality such as allowing for manual override may be introduced.

FIG. 1 is a block diagram 100 that illustrates an example of an internal database management system 102 for determining and applying address enhancements from address data. The internal database management system 102 obtains healthcare provider (HCP) records 132-1 through 132-N (collectively "HCP records 132") from external data sources 130-1 through 130-N (collectively "external data sources 130"). In some cases, external data sources 130 can also be referred to as "external sources." Other examples of external sources can include medical claims data, prescription data, etc. associated with HCPs, in which the external data sources 130 include HCP records 132 with addresses for the associated HCPs. The HCP records 132 can include data related to the healthcare provider such as the type of medical practice associated the address (e.g., private office, public organization, private hospital, public hospital). In some cases, the HCP records 132 also include medical license data for the healthcare provider, such as the licensing organization, licensing state, validity status of the license, and other types of licensing information. Prescription data can include includes medical prescriptions prescribed by the healthcare provider for healthcare provider's patients can be used to determine the accuracy of an address. The address of where a prescription is filled can indicate that addresses with the same geographical state or city are more accurate, e.g., the healthcare provider is actively providing medical care to patients by prescribing medication.

The internal database management system 102 is also configured to obtain evidence data 142-1 through 142-N (collectively "evidence data 142") from user devices 140-1 through 140-N (collectively "user devices 140"). The internal database management system 102 can be configured to generate outputs including address ranking data 160, a trend report 162, and an accuracy report 164 to client devices 152-1 through 152-N (collectively "client devices 152"). A client device 152 can include a user interface 154 configured to display any of the outputs provided by the internal database management system 102. In some cases, the internal database management system 102 can generate data that causes the user interface 154 to display an output, e.g., address ranking data 160, a trend report 162, and/or an accuracy report 164. In some implementations, data related to the address ranking such as the outputs of the internal database management system 102 (e.g., address ranking data 160, trend report 162, accuracy report 164) can be provided periodically or at a particular cadence.

The address ranking data 160 can include a list of addresses for a healthcare provider, including a ranking of the addresses. A ranking of addresses can include a sorting of addresses, from highest likelihood to lowest likelihood of the address being a correct address for the healthcare provider. The trend report 162 can include a summary of analyzed trends from external data sources 160, HCP records 132, and evidence data 142 determined by an address intelligence engine 104 of the internal database management system 102. Similarly, the accuracy report 164 can also include a summary of accuracy scores for different addresses determined by the address intelligence engine 104.

Although FIG. 1 depicts the internal database management system 102 obtaining a corresponding set of HCP records 132 from each external data source 130, any number of HCP records can be obtained from a particular external data source 130. In some cases, the internal database management system 102 can be configured to obtain select portions of the HCP records 132 from an external data source 130 that may be deemed as accurate address data, e.g., relative to the other portions of the HCP records 132 for the same external data source 130. In some implementations, the internal database management system 102 can be configured to skip collection of HCP records 132 from one or more particular external data sources 130, in response to determining that the particular external data sources are unlikely to include accurate address data. For example, some external sources such as volunteer healthcare organizations or collaborative research organizations may not demand address updates from a healthcare provider when the healthcare provider changes occupancy locations. Thus, the internal database management system 102 can determine that addresses from these types of external sources may not be accurate, e.g., on a volunteer basis. As another example, some external sources may include periodic communication with the healthcare provider to update and/or maintain address of record. In some implementations, external data sources 130 include an option for healthcare providers that allow the healthcare provider to opt-out of reporting addresses. Thus, the addresses from HCP records from these external data sources 130 can continue to report an address that is no longer accurate for the healthcare provider.

The internal database management system 102 is configured to obtain evidence data 142 from user devices 140, which include primary research (e.g., conducted by analysts) related to addresses stored in the internal address database 114. The primary research can independent verification of addresses through phone calls, correspondence, etc. In some implementations, the evidence data 142 can be utilized by the address intelligence engine 104 to remove addresses from the received HCP records 132 and/or internal addresses 116 or to otherwise indicate a low accuracy of certain addresses, e.g., e.g., as a first filter to identify the best address for a healthcare provider. For instance, if an analyst has direct contact with a healthcare provider who confirms that a certain address is outdated, this information is used to remove or otherwise indicate a low likelihood of accuracy of the address. In some cases, the evidence data 142 includes an activity status (e.g., practicing, retired, semi-retired, sabbatical, research fellowship) of a healthcare provider, through a phone call, institutional check, correspondence, etc.

The internal database management system 102 includes the address intelligence engine 104, which can be configured can apply techniques to determine the type (e.g., "Home," "Office," "Both," or "Unknown") of an address. As an example, the address intelligence engine 104 can implement rules from audit codes 122 for assignment of address types (e.g., assigning Home or Office) when an external data source 130 does not indicate a type for an address in the HCP records 132. For example, when a street front location has multiple distinct addresses for multiple HCPs, each of which is listed with an address line 2 of "Apt n," and there is no evidence indicating that any address at the street front is an Office, an audit rule 122 can direct that the address be marked as "Home." By identifying a type of an address, the address intelligence engine 104 can accurately characterize the address for output, e.g., to a service provider that can use an appropriate type of address to contact a healthcare provider. For example, a service provider can use addresses with an "Office" address type to efficiently contact a healthcare provider regarding office administration materials and services, whereas addresses with a "Home" address type can be used for communications regarding telehealth services, medical licensing, etc.

The address intelligence engine 104 can improve the usefulness and accuracy of addresses obtained from the HCP records 130 and the evidence data 142 (e.g., by ranking addresses based on accuracy scores). In some cases, multiple addresses can be associated to a healthcare provider based upon various reasons, such as changes due to pandemics or other types of events. These types of events can result in healthcare providers changing locations for their primary occupancy, e.g., where healthcare providers provide care and see patients. For example, some events can result in an increase in remote healthcare (e.g., telehealth) practices by a healthcare provider, relative to in-person healthcare practices conducted at a hospital, medical office, etc.

The address intelligence engine 104 includes an HCP record scoring module 106 that can perform a preliminary assessment of addresses in the HCP records 132. For example, the street fronts in addresses of the records can be added to the address and audit codes 122 can be applied to the addresses. For example, an audit code 122 associated with metro areas with apartment buildings can be applied to the address by incorporating address information (e.g., from medical claims information, licensing records, etc.) from other external sources (e.g., other databases, other types of sources) provided through HCP records 132. The HCP record scoring module 106 can detect conflicts detected and processed for addresses that are indicated as "Home" and "Office"; for example, the number of attempts to settle Home and Office conflicts may be lowered unless one or more clear-cut outliers are identified. Outliers can be determined from the evidence data 142 collected by user devices 140, in which the address intelligence engine 104 can be configured to apply evidence-based techniques. For example, if there is no evidence of an office, the platform will move the address to "Unknown" rather than "Both" ("Home" and "Office"). As another example, conflicts between different addresses can take form of noncontiguous geographical location, e.g., different states that can indicate a discrepancy in the healthcare provider's practice location. For instance, for the same healthcare provider, office addresses in both Montana and Florida may indicate that only one of these is a current accurate address. The address intelligence engine 104 can utilize one or both the HCP record 132 or the evidence data 142, along with the audit codes 122, to determine one or more addresses that are more likely to be accurate among the addresses reported for the healthcare provide.

The address intelligence engine 104 can be configured to utilize audit codes 122 for assigning "Home" or "Office" as an address type for an address. For example, the address intelligence engine 104 utilizes audit codes for addresses where the HCP record 132 from the external data source 130 does not indicate if the address is a home address or an office address. An audit code 122 can define a type of processing to be performed by the address intelligence engine 104, to process the address from the HCP record 132 when the HCP record does not indicate "Home" or "Office." In some cases, the type of processing can include identifying an address type utilizing a different HCP record (e.g., from a different external data source) than the HCP record 132 and external data source that the address originated from. Thus, the address intelligence engine 104 can be configured to adjust an address type using trends from different external data sources to accurately characterize the address type of an address. Based upon adjusting an address type for an address associated with a healthcare provider to an address type that accurately characterizes the address, improvements can be realized and quantified. For example, a considerable number of addresses (e.g., millions of addresses of a master address table) can shift to more specific and accurate data. Such adjustments can also increase the level of confidence for the addresses in the address ranking data 160 provided to the client devices 150.

The address intelligence engine 104 performs an initial validation of an internal address 116 from the internal address database 114 to compute an internal score (e.g., an accuracy of an address from an internal source). For example, the address intelligence engine 104 obtains internal addresses 116 for a healthcare provider and determines an internal accuracy score for each address, indicating a likelihood that the address is correctly associated with the healthcare provider. For example, the internal database scoring module 108 processes the internal addresses 116 from the internal address database 114 and determines a number of criteria describing a type, age, and any associated codes for the internal addresses 116. In some cases, the internal database scoring module 108 identifies designations for the internal addresses based on affiliations of the healthcare provider to one or more healthcare organizations. The internal database scoring module 108 utilizes the healthcare organization affiliations of the healthcare providers to designate a reliability and/or validation of the internal addresses 116 from the internal address database 114. For example, the internal database scoring module 108 can generate an internal score for an address for a healthcare provider associated with a first healthcare organization that is higher than an internal score for an address with a second healthcare organization that is known to be less accurate than the first healthcare organization. Some healthcare organizations update records less frequently than other healthcare organizations, e.g., volunteer healthcare organizations can update addresses infrequently compared to hospital healthcare organizations.

The address intelligence engine 104 determines an external score (e.g., an accuracy of an address from an external data source) by processing addresses from HCP records 132 using the HCP record scoring module 106. The HCP record scoring module 106 computes an external score of an HCP record indicating an adjustment of the accuracy for the HCP record 132, e.g., to increase or decrease a weighting of the addresses included in HCP record 132.

The HCP record scoring module 106 of the address intelligence engine 104 can be configured to perform preliminary analysis of the HCP record 132 to determine that the address data in the HCP record 132 has a likelihood of accurately characterizing the type of address for a particular type of healthcare professional. Multiple external data sources can each have a particular weighting, indicating an accuracy of the addresses from the respective external score. The weighting from the preliminary analysis performed by the HCP record scoring module 106 can be determined based on characteristics of the address data in the HCP records 132. The characteristics of the address data can include information embedded in the address data, metadata describing the address data, etc. For example, addresses from some external data sources include particular fields (e.g., healthcare provider role, certification date) for address data in HCP records 132, in which the field is likely to indicate that the address from an external data source 130 for which the HCP record 132 originated from is likely to be accurate. In some cases, trends of how and when particular fields in addresses are populated over a time period can indicate the accuracy of the address from the HCP record.

The weightings for HCP records determined by the HCP record scoring module 106 identify external data sources that are likely to improve stability and accuracy of resulting addresses for healthcare providers. For example, address enhancements can be achieved by emphasizing particular types of HCP records 132 with high-quality data and fidelity, over other types of HCP records 132 that includes address data that is likely to be inaccurate and/or low fidelity. By pre-processing and analyzing the HCP records 132, the address intelligence engine 104 can improve rates of detecting address data that result in false positive or false negative address assignments to a healthcare provider, including erroneous updates to addresses in the internal address database 114.

The address intelligence engine 104 is configured to apply the audit codes 122 from the audit codes database 120 for scoring the accuracy of addresses associated to each healthcare provider. For example, the application of audit codes 122 based on types of addresses can reduce usage of computational resources to update and enhance the information provided by an address, e.g., prioritizing an address based on an audit code. The application of audit codes 122 to addresses processed by the address intelligence engine 104 permit improved ranking for addresses of a healthcare provider, e.g., to determine addresses with highest likelihood of being associated to a location where the healthcare provider practices.

In some implementations, the address intelligence engine 104 of the internal database management system 102 can include a number of processing stages to perform address enhancement. The processing stages include an assessment of the status of an address, e.g., from HCP records 132, internal addresses 116. The number of processing stages can be configured based on a particular confidential interval for address ranking and/or enhancement, and thus various levels of computational savings and efficiency can be achieved. In some cases, the processing stages can be performed in any order, such as scoring of addresses from external data sources 130 before internal addresses 116 of the internal address database 114, or vice-versa. In some cases, the order of processing can be performed based on the type of HCP records 132 received from an external data source 130.

In some implementations, the address intelligence engine 104 applies multiple sets of audit codes 122 as overrides to the address rankings and scores, e.g., to identify and assign tags to the address data. In some cases, portions of the data can be tagged to indicate a score that describes affiliations between healthcare parties such as organizations, and healthcare practitioners, and the addresses in the address data. For example, an audit code 122 can include a tag "NEG_CD" (e.g., a negative audit code) can be assigned to an address (e.g., from HCP records 132 and/or internal addresses 116) that does not follow a particular rule. The tag can indicate that an address is transitional or old and provides a particular rank (e.g., a low ranking relative to other addresses for the healthcare provider) for the address. By assigning particular types of tags to addresses form the audit codes 122, data related to addresses from the HCP records 132 can be flagged accordingly. In some cases, the address intelligence engine 104 can process address data from the HCP records 132 based on the tags from the audit codes 122 to expedite accurate ranking of the addresses, as trends relating to associations between health care providers and addresses are determined.

In some implementations, tags from audit codes 122 can be associated with particular rules, each tag having a respective description indicating a type of address intelligence. For example, if a healthcare provider is indicated as inactive, then the addresses from HCP records 132 can be marked with particular tags can be removed, deleted, etc. to reduce processing loads when performing address updates from external data sources 130. Data related to particular healthcare providers can indicate that the healthcare provider is inactive, that the address data of the HCP records 132 is incomplete. By adding particular tags based on the audit codes 122 for the address data of the HCP records 132, the internal database management system 102 can handle large volumes of address updates by processing the addresses using the tags (e.g., descriptive codes and attributes for addresses) to rank the addresses for the healthcare provider.

As another example, the address intelligence engine 104 performs an internal scoring of internal addresses 116 by an internal database scoring module 108 and external scoring for address data from HCP records 132 by HCP record scoring module 106. The internal scoring and external scoring can indicate that the address for a healthcare provider can qualify for a particular rank (e.g., a cumulative number of points indicating high accuracy for an address). In some cases, addresses for healthcare providers can qualify for a particular range of ranks, to expedite updating and analysis of addresses, e.g., to provide client devices 150. In some implementations, address enhancements can be performed by leveraging some, but not all processing stages of the address enhancement techniques performed by the address intelligence engine 104, e.g., by filtering based on external scores only or internal scores only.

The address intelligence engine 104 can be configured to analyze sets of addresses using a trend analysis module 112 to identify trends in trustworthiness of sources. The trend analysis module 112 can allow the address intelligence engine 104 to identify an address with a highest likelihood of having the healthcare provider residing at said address by determining accuracy trends of various external data sources 130. For example, this can include determining accuracy scores for each external data source, or different combinations of external data sources, to identify changes in accuracy of the address data from the records of the sources. In some cases, the trend analysis module 112 computes time-series external scores representing accuracy of the external data sources 130. In some cases, the trend analysis module 112 computes trends that pertain characteristics of addresses, e.g., characteristics that render a given addresses more or less likely to be accurate.

In some implementations, trends from the trend analysis module 112 can be utilized to determine rules to rank addresses. Addresses can be ranked based on based on evidence data 142 (e.g., primary accuracy evidence from research through the user devices 140), or accuracy evidence from the external data sources 130. For example, external evidence from HCP records 132, e.g., from one or more external data sources 130, can indicate that an address should be removed when determining the best address. In this example, an address can omitted in ranking of addresses from the HCP records 132 if a particular location of the address is substantially different than other locations of other addresses for the same healthcare provider, e.g., different states/countries. In some cases, multiple override stages can be utilized by repeatedly applying rules to rank, as well as filter, addresses.

In some cases, some external data sources 130 may not be updated or renewed by a healthcare provider and thus the information (e.g., HCP records from the external sources) can have an accuracy that decays over time. For example, a healthcare professional may have a national healthcare provider identifier indicating an address that the healthcare provider practices at a particular address, which may not be updated when the healthcare professional moves or practices at a different address. Thus, the address intelligence engine 104 can determine a trend for records of external data source 130 that indicates low accuracy for particular types of healthcare providers that are likely to travel or move (e.g., traveling nurses, medical residents, medical students, semi-retired professionals).

In some implementations, trends within an external data source 130 can be determined by sampling a record from a source by a professional activity, indicating a type of role performed by the healthcare professional. For example, the professional activity type can indicate that the healthcare provider is a researcher, semi-retired, full-time hospital staff, office-based, or any type of activity that provides another characterization of the accuracy for the address of the healthcare provider in the record. As another example, a professional activity type for a mid-level healthcare professional can indicate that the healthcare professional is more likely to be office-based addresses, compared to semi-retired or retired healthcare providers who are more likely to use P.O. Box addresses to receive mail, e.g., less likely to be associated with a particular office or infrequently practice medicine at the same location.

The internal database scoring module 108 can compute an internal score for an address from the internal address 116 based on characteristics of the data, e.g., the originating source of the data, the age of the data, etc. For example, internal scoring of the internal addresses 116 using an address characteristic (e.g., including the address itself) can indicate that the address for the healthcare provider may require substantial updates in a particular pattern to override the ranking of the address. Therefore, by assigning the initial ranking, e.g., the initial score, the address can be efficiently acknowledged by the address intelligence engine 104 to avoid extraneous address updates, e.g., resulting in additional expenditure of computational resources. Through performing initial validation of the address intelligence techniques, the internal database management system 102 can be configured to identify updates in healthcare provider data, affiliation, and addresses.

In some implementations, the address intelligence engine 104 adjusts an accuracy score for an address based on one or both of relationships between different HCP records 132 for a healthcare provider, an applicability of an accuracy trend for an external source of the address. For example, a score can be assigned based on different HCP records that share some similarities in address information, address format, source origin, source age, source type, etc. The score can indicate an increased likelihood of accuracy, e.g., if the same address appears in multiple records from different sources. The score can also indicate a decreased likelihood of accuracy, e.g., if information in one record indicates lack of accuracy of an address in another record. For instance, if an address from a professional organization indicates that an HCP's address is in New Hampshire, but a record from a New Hampshire licensing database indicates that the HCP's New Hampshire license has expired, this can be used to decrease the accuracy score of the HCP's New Hampshire address.

In some implementations, an accuracy score can be assigned by selecting a combination of different parts of HCP records 132 with a trend measured by the address intelligence engine 104. In some implementations, the address intelligence engine 104 applies an accuracy trend to the address to determine a correlation between the address and the trend for the source, e.g., indicating whether or not the trend applies to the address and its associated source.

In some implementations, the trend is time-based, e.g., indicating a decay in accuracy of addresses over time. In some implementation, the trend is based on address characteristics. For instance, a given data source may be observed to have an average of 70% of its addresses being accurate. Based on analysis of the addresses from the data source, a trend can be identified indicative of which address characteristics correlate with a given address being in that 70% of accurate addresses. For instance, an analysis may indicate that doctor addresses tend to be less accurate than nurse addresses, or that hospital-based providers tend to be more accurate than academic HCPs. This trend can be used to determine the likelihood that a given address from that source is accurate, and to assign an accuracy score accordingly.

In some implementations, the internal database scoring module 108 computes an internal score based on the evidence data 142 to compute an accuracy of the validity of an address and an age, e.g., a length of time. The age of an address describes an instance of when the address was first valid for a healthcare provider. In some implementations, the evidence data 142 can include validation from phone calls, websites, correspondence, etc. The internal score can include a breakdown of evidence 142 based on age, with respective numerical and/or categorical weightings for different ages of addresses. For example, the weightings for an address can be greater for an address that is more recent compared to another address that was validated at an older age. In some cases, the evidence data 142 can include an initial evaluation of an address, e.g., indicating that the address is a primary location for a healthcare provider. In some implementations, the evidence data 142 can include designations indicating a likelihood of an address being associated to a healthcare provider. Data from primary research such as likelihoods and weightings can be stored in data structures, e.g., matrices, vectors, tensors, etc.

Referring to the HCP records 132, the HCP record scoring module 106 can be configured to perform external data source tagging of the HCP records 132. For example, the HCP record scoring module 106 can apply a number of tests (e.g., rules) on the HCP records 132 based on the audit codes 122 from the audit codes database 120 to determine an external score for the respective HCP record 132. The data (e.g., address data, claims data) of the HCP records 132 can be sampled and analyzed using any number of pre-processing operations, e.g., to boost some types of address data over other types of address data. In some cases, raw data from the HCP records 132 can be processed to indicate a record of all healthcare provider addresses across all HCP records 132 for a healthcare provider. The raw data from the HCP records 132 can be further processed (e.g., by the HCP record scoring module 106) based on the age of the date, to indicate a weighting that corresponds to how recent the address data was recorded. For example, point values can be assigned to weigh some parts of the address data more than other parts of the data from an older time period, date, etc. As another example, calculations for the external score of the HCP records 132 can include incorporating statistics related to the HCP record 132 from an external data source, among the external data sources 130, to provide metadata, statistical data, etc. for the address. In other words, patterns identified in a type of HCP record 132 can be applied to identify the reliability and accuracy of a particular address in a HCP record 132.

In some implementations, the trend analysis module 112 can be configured to track accuracy trends by applying tags (also referred to as "external tags") to the HCP records 132. For example, external tags for HCP records 132 can indicate the age of a source upon termination of when an external data source no longer reports HCP records 132. By doing so, an age of the HCP record 132 can be tracked and leveraged to identify more recent sources than aging sources. In some implementations, the address intelligence engine 104 can be configured to perform an auditing process adjust an accuracy score of the HCP records 132 based on the external tags, i.e., an overriding audit code 122 being applied to the address to assign a different ranking to address. In some implementations, audit codes 122 by the address intelligence engine 104 can be triggered apply a particular adjustments in accuracy of an HCP record 132. The audit codes 122 can indicate a triggering condition of that one or both the HCP record 132, evidence data 142, satisfy, or violate.

In some implementations, the address intelligence engine 104 performs a preliminary ranking process of addresses. The preliminary ranking process can be applied to incorporate internal accuracy scores (e.g., from analyzing internal addresses 116) and external scores (e.g., from analyzed HCP records 132) to provide an initial ranking of an address among other addresses for a healthcare provider. For example, the preliminary rank assigned to an address among multiple addresses provided for a healthcare provider can permit identification of differences and reliability of an HCP record 132 from one external data source 132 to another external data source 132. The preliminary rank of an address can be further adjusted by the address intelligence engine 104 by categorizing addresses into subsets of ranks or groupings of ranks. Each subset of ranks can be processed, e.g., by applying by one or more audit codes 122 from the audit codes database 120 to expedite processing, analysis, and updating of the address.

In some implementations, the address intelligence engine 104 samples addresses for a particular types of healthcare provider across different external data sources 130. The sampling of an address across data sources can provide a preliminary analysis of the accuracy and overall data fidelity of a particular external data source 130 by comparing the address to different sources that include the same address.

By providing further granularity through the type of healthcare provider, addresses associated with particular types of healthcare providers can be accurately described by patterns and trends in the data, e.g., by the trend analysis module 112. For example, a traveling nurse may be more likely to have multiple types and instances of addresses, compared to supervisory nursing staff who are more likely to spend more time at one particular address. Furthermore, the level of stratified sampling provided by the address intelligence engine 104 (e.g., by determining trends at the healthcare provider level) can further include a high-level representation of the accuracy by provider type, which can be filtered accordingly. In some implementations, a sampling of an HCP record 132 can indicate an accuracy pattern from external data sources 130 to indicate address preferences. A quantitative scoring of the address can include adjusting parameters to improve updating address rankings through address updates 118. In some implementations, subgroupings (e.g., a type of healthcare provider, a type of source) of HCP records 132 can be identified and scored independently, thereby allowing pattern identification within a subgroup and across different subgroups. Features of addresses from the group of HCP records 132 can be boosted or decremented based on features from the subgroupings, e.g., to improve address rankings and accuracy.

In some implementations, the preliminary ranking performed by the address intelligence engine 104 can include a ranking of subgroups, e.g., based on a type of healthcare provider. Each type of grouping and source can be classified based on a likelihood indicating accuracy of an address. In some implementations, rankings for addresses can various accumulations of points that correspond to an accuracy weighting for the address. For example, an address with a high ranking can accumulate more points than addresses with lower assigned ranks.

In some implementations, the address intelligence engine 104 perform source testing of external data sources 130 to determine an "external point" or "external score". An external data source 130 can be evaluated to compute a number of external points representing accuracy of the external data source determined by the address intelligence engine 104. For example, a type of external data source 130 and its related addresses, e.g., from HCP records 132 can be analyzed to determine the accuracy of the external data source in its entirety.

The trend analysis module 112 is configured to determine trends in accuracy, fidelity, stability, and other characteristics for a data source that can indicate likelihood of similar characteristics in the addresses for a healthcare provider. In some cases, this can include a time-series analysis of address accuracy of the external data source, which can include analyzing time/date of address data received, time/data of address data recorded, and so on. From analyzing time-series accuracy scores of addresses, the address intelligence engine 104 can identify that particular types of HCP records 132 that indicate likelihood of having an address that is inactive, not classified, semi-retired, etc.

As an example, the HCP record 132 for an individual external data source 130 can be tested and assigned source tags (also referred to as external source tags) that can be used to assign a baseline number of points associated for the external data source 130, e.g., a matrix of values. The matrix of values can describe a baseline accuracy for an address provided by the external data source 130, e.g., through the reference file. In more detail, a matrix of values can be generated when determining an internal score for an internal address that matches an address from the HCP record 132, which can be based on one or more designations for external data source for the HCP record 132. The entries in a matrix representing can be updated, e.g., continually, periodically, etc. as addresses are updated across multiple instances. As external points are determined for different external data sources 130, the matrix of values can be updated, e.g., by increasing or decreasing the values. The external points can indicate that a type of external data source 130 can be weighed as more accurate than another type of external data source 130 source, in which the external points derived from tags of the respective external data source 130 provide additional context to rank addresses.

In some examples, the external points for an external data source 130 can be assigned on an age basis of the source, an indication of a particular activity of the healthcare provider corresponding to the address, etc. In some implementations, the address intelligence techniques described herein can implement address enhancement by boosting or decrementing external data source 130 based on the external points, which can be established by tagging the HCP records 132 for the external data source 130.

In some implementations, HCP records 132 can be assigned with tags indicating a particular way to process the record based on the source, e.g., age of source, type of source, as a form of source tag audit processing. The source tag audit processing provides that different rules can be applied to an external data source to adjust the scoring of the source. By adjusting the scoring, further computational benefits can be achieved to emphasize some types of sources over other types of sources. In some implementations, the address intelligence engine 104 can generate audit codes indicating that sources have a particular status, e.g., downgraded, standard, voided, etc. As an example, sources that are downgraded can be based on having a relatively short age, e.g., one year, and can indicate that source is yet to be a reliable source (e.g., with statistical significance) for addresses, address updating, and generally improving the address characteristics.

The address intelligence engine 104 can update addresses of the internal address database 114 based on address updates 118. The address updates 118 can be based on internal scoring of the internal addresses 116, external scoring of addresses from the HCP records 132, and identified trends from the trend analysis module 112. For example, the address intelligence engine 104 can determine that based on a high ranking of an address (e.g., from internal and/or external points) relative to other addresses, that an update to an address can be made in the internal address database 114. Addresses, including their associated rankings, can be stored in the internal address database 114.

The address intelligence engine 104 can identify one or more audit codes that correspond to rules specifying types of sources that follow particular patterns. The patterns can be an example of the source having statistically relevant features indicating that the source is reliable and accurate for associating healthcare providers to the addresses from the HCP records of the source. In some implementations, the address intelligence techniques performed by address intelligence engine 104 can include identifying patterns that achieve benefits such as reducing the likelihood of false positive, false negative, and balancing between the two advantages without increasing a computational burden for the internal database management system 102 for updating addresses. In some implementations, rules from the audit codes 122 can be learned over periods of time identify combinations of features of the HCP records 132, and/or the evidence data 140 to determine best addresses associated with the healthcare provider, even when the healthcare provider is associated with multiple instances of different addresses, address formats, etc. An audit code from the audit codes 122 can specify a condition, or combination of conditions, for an address from a data source (e.g., internal sources, external sources). The accuracy score for an address can be adjusted based on the address satisfying or violating an audit code from the audit codes 122. Examples of conditions can include the address format, content, and data related to the external source type, origin, age, etc.

In some implementations, the address intelligence engine 104 is configured to determine likelihoods of addresses corresponding to a healthcare provider and/or professional. For example, the process can include applying sets of audit codes 122 to continually filter to a best address, e.g., an address with the highest likelihood of association to a healthcare provider. In some implementations, address conflicts with similar rankings, e.g., two addresses at the same ranking, can be de-conflicted to identify a single best address based on one or more audit code. The audit codes 122 from the audit codes database 120 that de-conflict between two or more addresses with the same ranking be based on address descriptors, which are characteristics about the address and its ranking that can inform which of the multiple addresses should be ranked higher than the other remaining addresses. For example, some audit codes for de-conflicting addresses can be based on the source type of the addresses (e.g., internal source of an address from an internal database vs. external data source) and the type of information utilized in an address (e.g., portions of the address indicating a type of address).

Figure 2:
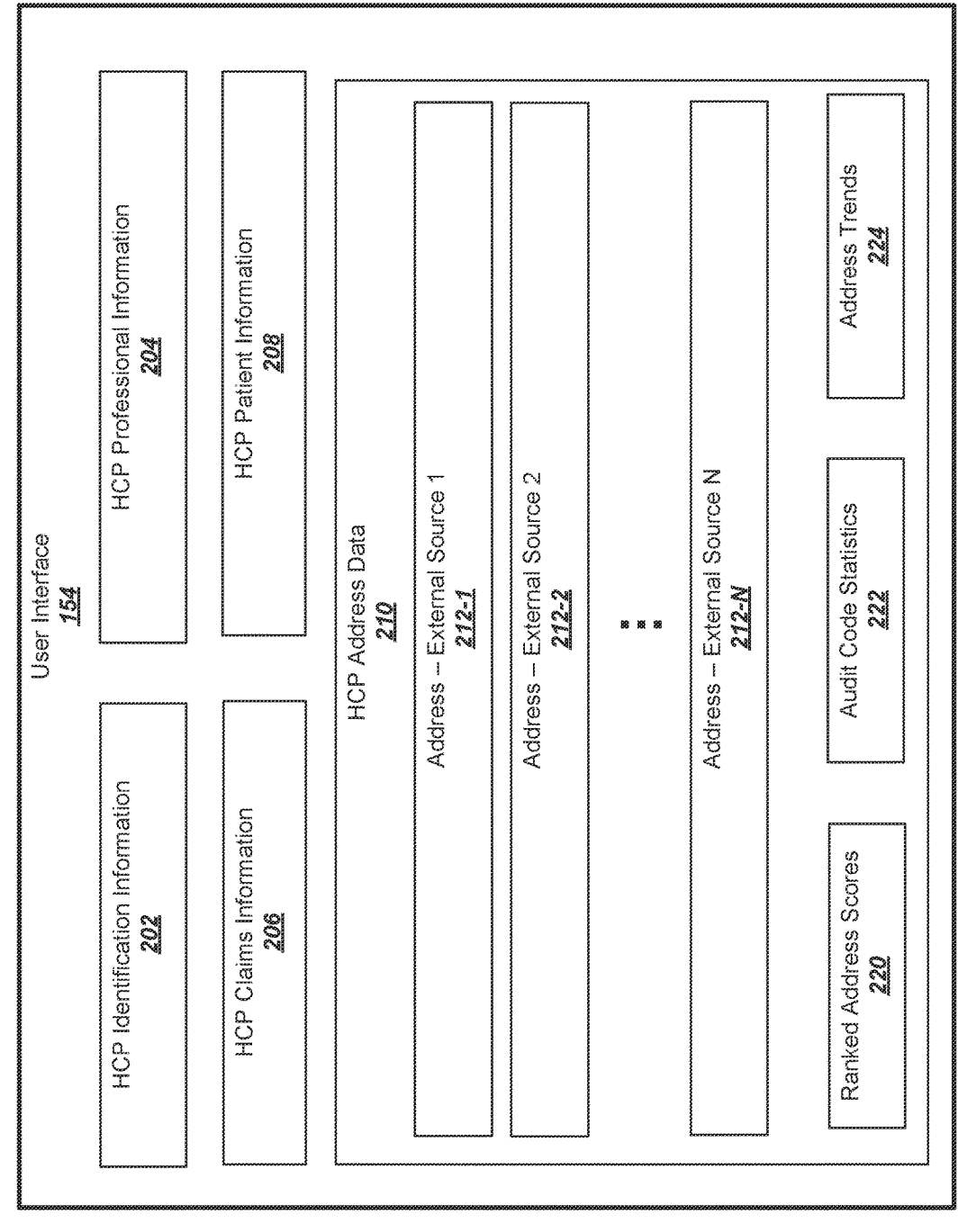
FIG. 2 is a block diagram that illustrates an example of a user interface displaying address enhancements.

FIG. 2 is a block diagram 200 that illustrates an example of user interface 154 displaying enhanced address data. The diagram 200 depicts the user interface 154 of FIG. 1 with multiple windows indicating information provided by the address intelligence engine 204. For example, the user interface 154 shows identification information 202, professional information 204, claims information 206, and patient information 208, for one or more healthcare providers. The identification information 202 can include information that identifies the healthcare provider such as name, age, sex, and other personally identifiable factors that uniquely identify the healthcare professional from other professionals. The professional information 204 can include a type of healthcare role, types of degrees granted, names of institutions associated with the healthcare provider, practice status (e.g., retired, active, research fellowship) and other types of professional data. The claims information 206 can include insurance claims, prescriptions, and other types of medical claim statistics associated with the healthcare provider, while the patient information 208 indicate data about the healthcare provider's practice with their patients, such as number of associated patients, patient visits, etc.

The block diagram 200 also depicts the user interface 154 displaying address data 210 for the healthcare provider. The address data includes addresses 212-1 through 212-N (collectively "addresses 212") from different external data sources, e.g., external data source 130-1 through 130-N. A window of the user interface 154 for an address 212 includes information about the address from the external data source, such as address line 1, address line 2, city, state, zip code. The window of the user interface 154 for the address 212 can also include metadata for the address from the external data source, such as the recency of the address reporting from the source, the instance of when the address was first reported by the external data source, and other characteristics about the address.

The block diagram 200 also depicts the user interface 154 displaying ranked address scores 220, audit code statistics 222, and address trends 224. The ranked address scores 220 can include accuracy scores for each address 212 displayed on the user the interface, and statistics relating to the scores, e.g., an average score, median score, minimum score, maximum score. The user interface 154 can also display audit code statistics 222 that summarize different audit codes and rules applied to the external sources from data analyzed by the address intelligence engine 204. In some cases, the audit codes can be categorized by type, e.g., an audit code that indicates the address as accurate or inaccurate, and/or assigns a particular type based on an override. The address trends 224 can include time-series values of accuracy for an external data source over time, e.g., demonstrating improvements or declines to accuracy of addresses from records of the external data source.

FIG. 3 is a flow diagram that illustrates an example of a process 300 for identifying accurate addresses from healthcare provider records, which can include ranking addresses to provide a best address for a healthcare provider, e.g., the highest likelihood of association with the healthcare provider. The process 300 can be performed, for example, by the internal database management system 102, the address intelligence engine 104, which can include one or more computers, illustrated in FIG. 1. The internal database management system 102 can be referred to as a computer system with one or more processors, which can be configured to perform the process 300.

The process 300 includes obtaining multiple records for a health care provider from one or more sources, each record specifying an address for the health care provider (310). Examples of records can include HCP records 132, described in reference to FIG. 1 above, and the records for a healthcare provider can be obtained from external sources, e.g., external sources 130.

The process 300 includes assigning an accuracy score to each address based on (i) relationships among at least some of the multiple records for the health care provider or (ii) applicability, to the address, of an accuracy trend for the source of the address (320). The accuracy score assigned to an address can be assigned based on an age of the address from the record. In some implementations, the relationships among the at least some of the multiple records can be determined by identifying a key value linking the records. In some implementations, determining the applicability of the accuracy trend to a given address is based on a value in the record specifying the given address.

In some implementations, the accuracy trend for a source indicates a likelihood that an address from that source is accurate. Assigning the accuracy score for a particular address from a given source can include determining the applicability of the likelihood for the given source to the particular address.

The process 300 includes adjusting the accuracy score for each one or more of the addresses based on applying one or more audit rules to the address, each audit rule specifying an adjustment to the accuracy score based on a value in the record for the address satisfying or violating the audit rule (330). In some implementations, applying the one or more audit rules is based on a type of each of the addresses. The process can include identifying a type of each address, and in some cases, identifying the type of each address is based on evidence in the corresponding record indicative of the type of address. In some implementations, in the absence of evidence indicative of the type of address for a given address, the process 300 includes categorizing the given address as an unknown type. In some implementations, applying the one or more audit rules to a given address based on a type of occupation of the health care provider.

The process 300 includes storing the addresses for the health care provider and a ranking for each of the addresses, the ranking determined based on the relative adjusted accuracy scores of the addresses (340). For example, the address rankings can be stored in a data storage of a computer system.

The process 300 includes providing, for display on a user interface, data indicative of the ranking of the addresses (350). In some implementations, the user interface can be configured to display information related to a healthcare provider identification, professional status, medical claims associated to the healthcare provider, or information related to patients associated to the healthcare providers. In some implementations, the user interface is configured to display ranked addresses, their corresponding accuracy scores, statistics relating to the audit codes utilized to rank the addresses (e.g., how often each audit code is invoked), and address trends. The user interface can be configured to display trends representing address accuracy over time for an external source, multiple external sources, or some combination thereof.

In some implementations, the process 300 includes identifying the type of each address based on a rule specifying assessment of street front addresses. Identifying the type of each address can include resolving a conflict between multiple types of addresses identified for the address.

Figure 4:
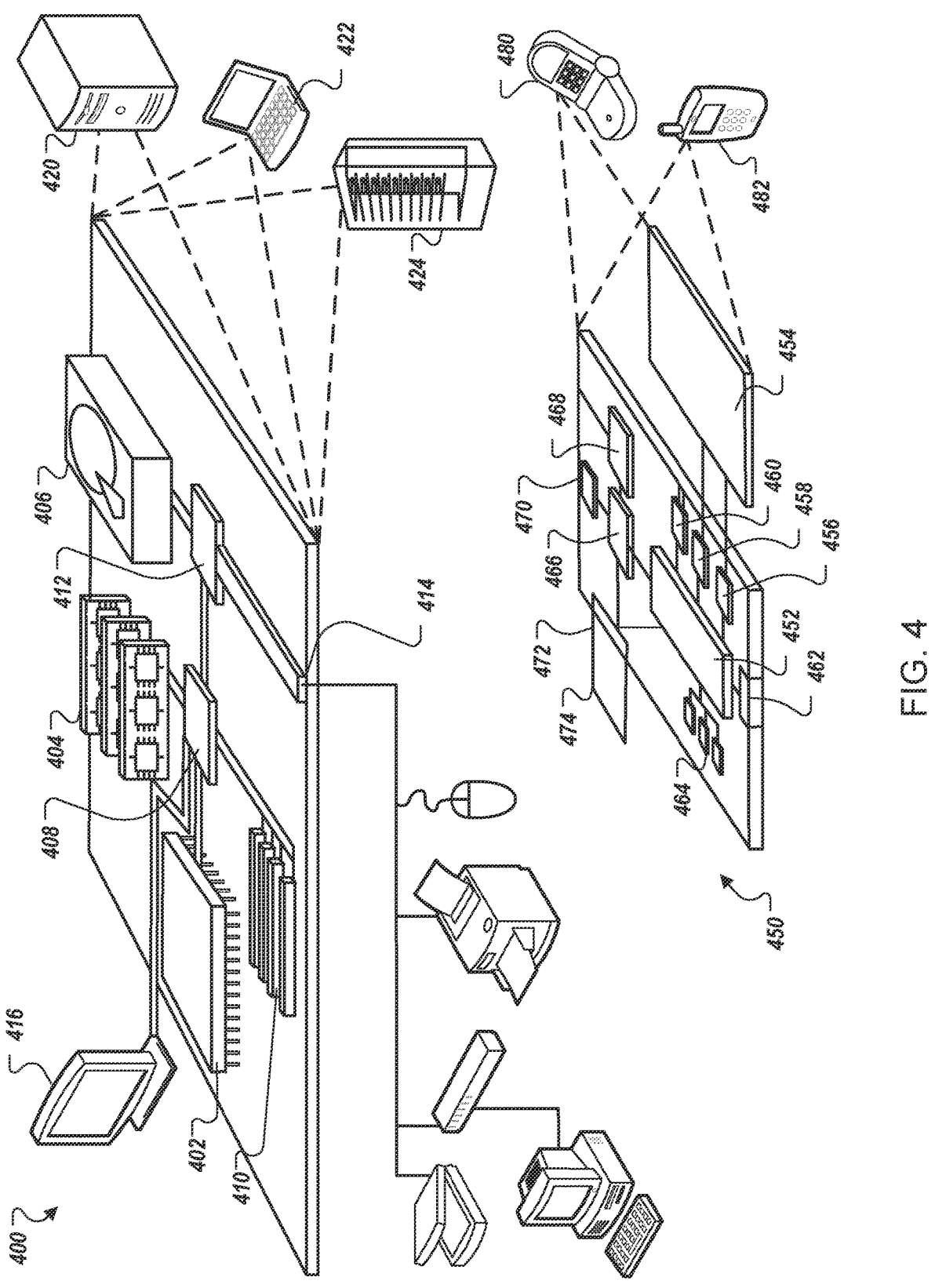
FIG. 4 shows a block diagram of a computing system.

FIG. 4 is a diagram illustrating an example of a computing system for providing and enhancing address intelligence. The computing system includes computing device 400 and a mobile computing device 450 that can be used to implement the techniques described herein. For example, one or more components of the internal database management system 102, the client devices 150, and/or the user devices 140, can be an example of the computing device 400 or the mobile computing device 450.

The computing device 400 is intended to represent various forms of digital computers, such as laptops, desktops, workstations, personal digital assistants, servers, blade servers, mainframes, and other appropriate computers. The mobile computing device 450 is intended to represent various forms of mobile devices, such as personal digital assistants, cellular telephones, smart-phones, mobile embedded radio systems, radio diagnostic computing devices, and other similar computing devices. The components shown here, their connections and relationships, and their functions, are meant to be examples only and are not meant to be limiting.

The computing device 400 includes a processor 402, a memory 404, a storage device 406, a high-speed interface 408 connecting to the memory 404 and multiple high-speed expansion ports 410, and a low-speed interface 412 connecting to a low-speed expansion port 414 and the storage device 406. Each of the processor 402, the memory 404, the storage device 406, the high-speed interface 408, the high-speed expansion ports 410, and the low-speed interface 412, are interconnected using various buses, and may be mounted on a common motherboard or in other manners as appropriate. The processor 402 can process instructions for execution within the computing device 400, including instructions stored in the memory 404 or on the storage device 406 to display graphical information for a Graphical User Interface (GUI) on an external input/output device, such as a display 416 coupled to the high-speed interface 408. In other implementations, multiple processors and/or multiple buses may be used, as appropriate, along with multiple memories and types of memory. In addition, multiple computing devices may be connected, with each device providing portions of the operations (e.g., as a server bank, a group of blade servers, or a multi-processor system). In some implementations, the processor 402 is a single threaded processor. In some implementations, the processor 402 is a multi-threaded processor. In some implementations, the processor 402 is a quantum computer.

The memory 404 stores information within the computing device 400. In some implementations, the memory 404 is a volatile memory unit or units. In some implementations, the memory 404 is a non-volatile memory unit or units. The memory 404 may also be another form of computer-readable medium, such as a magnetic or optical disk.

The storage device 404 is capable of providing mass storage for the computing device 400. In some implementations, the storage device 406 may be or include a computer-readable medium, such as a floppy disk device, a hard disk device, an optical disk device, or a tape device, a flash memory or other similar solid-state memory device, or an array of devices, including devices in a storage area network or other configurations. Instructions can be stored in an information carrier. The instructions, when executed by one or more processing devices (for example, processor 402), perform one or more methods, such as those described above. The instructions can also be stored by one or more storage devices such as computer- or machine-readable mediums (for example, the memory 404, the storage device 406, or memory on the processor 402). The high-speed interface 408 manages bandwidth-intensive operations for the computing device 400, while the low-speed interface 412 manages lower bandwidth-intensive operations. Such allocation of functions is an example only. In some implementations, the high speed interface 408 is coupled to the memory 404, the display 416 (e.g., through a graphics processor or accelerator), and to the high-speed expansion ports 410, which may accept various expansion cards (not shown). In the implementation, the low-speed interface 412 is coupled to the storage device 406 and the low-speed expansion port 414. The low-speed expansion port 414, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. In addition, it may be implemented in a personal computer such as a laptop computer 422. It may also be implemented as part of a rack server system 424. Alternatively, components from the computing device 400 may be combined with other components in a mobile device, such as a mobile computing device 450. Each of such devices may include one or more of the computing device 400 and the mobile computing device 450, and an entire system may be made up of multiple computing devices communicating with each other.

The mobile computing device 450 includes a processor 452, a memory 464, an input/output device such as a display 454, a communication interface 466, and a transceiver 468, among other components. The mobile computing device 450 may also be provided with a storage device, such as a micro-drive or other device, to provide additional storage. Each of the processor 452, the memory 464, the display 454, the communication interface 466, and the transceiver 468, are interconnected using various buses, and several of the components may be mounted on a common motherboard or in other manners as appropriate.

The processor 452 can execute instructions within the mobile computing device 450, including instructions stored in the memory 464. The processor 452 may be implemented as a chipset of chips that include separate and multiple analog and digital processors. The processor 452 may provide, for example, for coordination of the other components of the mobile computing device 450, such as control of user interfaces, applications run by the mobile computing device 450, and wireless communication by the mobile computing device 450.

The processor 452 may communicate with a user through a control interface 458 and a display interface 456 coupled to the display 454. The display 454 may be, for example, a TFT (Thin-Film-Transistor Liquid Crystal Display) display or an OLED (Organic Light Emitting Diode) display, or other appropriate display technology. The display interface 456 may include appropriate circuitry for driving the display 454 to present graphical and other information to a user. The control interface 458 may receive commands from a user and convert them for submission to the processor 452. In addition, an external interface 462 may provide communication with the processor 452, so as to enable near area communication of the mobile computing device 450 with other devices. The external interface 462 may provide, for example, for wired communication in some implementations, or for wireless communication in other implementations, and multiple interfaces may also be used.

The memory 464 stores information within the mobile computing device 450. The memory 464 can be implemented as one or more of a computer-readable medium or media, a volatile memory unit or units, or a non-volatile memory unit or units. An expansion memory 474 may also be provided and connected to the mobile computing device 450 through an expansion interface 472, which may include, for example, a SIMM (Single In Line Memory Module) card interface. The expansion memory 474 may provide extra storage space for the mobile computing device 450, or may also store applications or other information for the mobile computing device 450. Specifically, the expansion memory 474 may include instructions to carry out or supplement the processes described above, and may include secure information also. Thus, for example, the expansion memory 474 may be provided as a security module for the mobile computing device 450, and may be programmed with instructions that permit secure use of the mobile computing device 450. In addition, secure applications may be provided via the SIMM cards, along with additional information, such as placing identifying information on the SIMM card in a non-hackable manner.

The memory may include, for example, flash memory and/or NVRAM memory (nonvolatile random access memory). In some implementations, instructions are stored in an information carrier such that the instructions, when executed by one or more processing devices (e.g., processor 452), perform one or more methods, such as those described above. The instructions can also be stored by one or more storage devices, such as one or more computer or machine-readable mediums (for example, the memory 464, the expansion memory 474, or memory on the processor 452). In some implementations, the instructions can be received in a propagated signal, for example, over the transceiver 468 or the external interface 462.

The mobile computing device 450 may communicate wirelessly through the communication interface 466, which may include digital signal processing circuitry in some cases. The communication interface 466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), LTE, 3G/4G cellular, among others. Such communication may occur, for example, through the transceiver 468 using a radio frequency. In addition, short-range communication may occur, such as using a Bluetooth, Wi-Fi, or other such transceiver (not shown). In addition, a GPS (Global Positioning System) receiver module 470 may provide additional navigation- and location-related wireless data to the mobile computing device 450, which may be used as appropriate by applications running on the mobile computing device 450.

The mobile computing device 450 may also communicate audibly using an audio codec 460, which may receive spoken information from a user and convert it to usable digital information. The audio codec 460 may likewise generate audible sound for a user, such as through a speaker, e.g., in a handset of the mobile computing device 450. Such sound may include sound from voice telephone calls, may include recorded sound (e.g., voice messages, music files, among others) and may also include sound generated by applications operating on the mobile computing device 450.

The mobile computing device 450 may be implemented in a number of different forms, as shown in the figure. For example, it may be implemented as a cellular telephone 480. It may also be implemented as part of a smart-phone 482, personal digital assistant, or other similar mobile device.

A number of implementations have been described. Nevertheless, it will be understood that various modifications may be made without departing from the spirit and scope of the disclosure. For example, various forms of the flows shown above may be used, with steps re-ordered, added, or removed.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively in communication to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads. Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network.

Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by a computing system, the method comprising:

obtaining, by one or more processors of the computing system, multiple records for a health care provider from one or more sources, each record specifying an address for the health care provider;

by the one or more processors, assigning an accuracy score to each address based on applicability, to the address, of an accuracy trend for the source of the address, wherein the accuracy trend represents accuracy of addresses stored in the source of the address over a defined period of time;

by the one or more processors, adjusting the accuracy score for each one or more of the addresses based on applying one or more audit rules to the address, the one or more audit rules representing incremental factors for adjusting accuracy scores of an address, each audit rule specifying an adjustment to the accuracy score based on a value in the record for the address satisfying or violating the audit rule;

storing, in a data storage of the computing system, the addresses for the health care provider and a ranking for each of the addresses, the ranking determined based on the adjusted accuracy scores of the addresses; and providing, for display on a user interface, data indicative of the ranking of the addresses.

2. The method of claim 1, comprising assigning the accuracy score to each address based further on an age of the address.

3. The method of claim 1, comprising determining the applicability of the accuracy trend to a given address based on a value in the record specifying the given address.

4. The method of claim 1, in which the accuracy trend for a source indicates a likelihood that an address from that source is accurate; and in which assigning the accuracy score for a particular address from a given source comprises determining the applicability of the likelihood for the given source to the particular address.

5. The method of claim 1, wherein assigning the accuracy score comprises determining a relationship among at least some of the multiple records for the health care provider, wherein the relationship is determined by identifying a key value linking the records.

6. The method of claim 1, comprising applying the one or more audit rules based on a type of each of the addresses.

7. The method of claim 6, comprising identifying a type of each address.

8. The method of claim 7, comprising identifying the type of each address based on evidence in the corresponding record indicative of the type of address.

9. The method of claim 8, comprising, in the absence of evidence indicative of the type of address for a given address, categorizing the given address as an unknown type.

10. The method of claim 7, comprising identifying the type of each address based on a rule specifying assessment of street front addresses.

11. The method of claim 7, in which identifying the type of each address comprises resolving a conflict between multiple types of addresses identified for the address.

12. The method of claim 1, comprising applying the one or more audit rules to a given address based on a type of occupation of the health care provider.

13. An address intelligence system comprising:

a computing device comprising at least one processor; and a memory communicatively coupled to the at least one processor, the memory storing instructions which, when executed by the at least one processor, cause the at least one processor to perform operations comprising:

obtaining, by the at least one processor, multiple records for a health care provider from one or more sources, each record specifying an address for the health care provider;

assigning, by the at least one processor, an accuracy score to each address based on applicability, to the address, of an accuracy trend for the source of the address, wherein the accuracy trend represents accuracy of addresses stored in the source of the address over a defined period of time;

adjusting, the at least one processor, the accuracy score for each one or more of the addresses based on applying one or more audit rules to the address, the one or more audit rules representing incremental factors for adjusting accuracy scores of an address, each audit rule specifying an adjustment to the accuracy score based on a value in the record for the address satisfying or violating the audit rule;

storing, in a data storage of the computing device, the addresses for the health care provider and a ranking for each of the addresses, the ranking determined based on the adjusted accuracy scores of the addresses; and providing, for display on a user interface, data indicative of the ranking of the addresses.

14. The system of claim 13, the operations further comprising:

assigning the accuracy score to each address based further on an age of the address.

15. The system of claim 13, the operations further comprising:

determining the applicability of the accuracy trend to a given address based on a value in the record specifying the given address.

16. The system of claim 13, in which the accuracy trend for a source indicates a likelihood that an address from that source is accurate; and in which assigning the accuracy score for a particular address from a given source comprises determining the applicability of the likelihood for the given source to the particular address.

17. The system of claim 13, wherein assigning the accuracy score comprises determining a relationship among at least some of the multiple records for the health care provider, wherein the relationship is determined by identifying a key value linking the records.

18. The system of claim 13, the operations further comprising:

applying the one or more audit rules based on a type of each of the addresses.

19. The system of claim 13, the operations further comprising:

identifying a type of each address.

20. The system of claim 13, the operations further comprising:

applying the one or more audit rules to a given address based on a type of occupation of the health care provider.

* * * * *